(12) United States Patent
Gut

(10) Patent No.: US 11,821,753 B2
(45) Date of Patent: Nov. 21, 2023

(54) METHOD FOR DETERMINING AN ORIENTATION OF A MOVABLE DEVICE

(71) Applicant: Robert Bosch GmbH, Stuttgart (DE)

(72) Inventor: Juergen Gut, Tuebingen (DE)

(73) Assignee: ROBERT BOSCH GMBH, Stuttgart (DE)

(*) Notice: Subject to any disclaimer, the term of this patent is extended or adjusted under 35 U.S.C. 154(b) by 708 days.

(21) Appl. No.: 16/978,038

(22) PCT Filed: Mar. 14, 2019

(86) PCT No.: PCT/EP2019/056385
§ 371 (c)(1),
(2) Date: Sep. 3, 2020

(87) PCT Pub. No.: WO2019/233644
PCT Pub. Date: Dec. 12, 2019

(65) Prior Publication Data
US 2021/0041264 A1  Feb. 11, 2021

(30) Foreign Application Priority Data

Jun. 7, 2018 (DE) .................. 10 2018 209 012.2

(51) Int. Cl.
*G01N 27/72* (2006.01)
*G01C 23/00* (2006.01)
(Continued)

(52) U.S. Cl.
CPC ............ *G01C 23/00* (2013.01); *A61B 5/1126* (2013.01); *A61B 5/6801* (2013.01); *A61B 2562/0219* (2013.01); *A61B 2562/0223* (2013.01)

(58) Field of Classification Search
CPC ............ G01R 33/0082; G01R 33/0206; G01V 3/081; G01P 15/18; G01P 1/023;
(Continued)

(56) References Cited

U.S. PATENT DOCUMENTS

2013/0155562 A1* 6/2013 Kubota ............... F02D 11/106
361/91.5
2013/0310711 A1* 11/2013 Wang ................... A61B 5/4528
600/595
(Continued)

FOREIGN PATENT DOCUMENTS

DE  102009019767 A1  11/2010
DE  102013000783 A1  7/2014
DE  102016009667 A1  4/2017

OTHER PUBLICATIONS

International Search Report for PCT/EP2019/056385, dated Jun. 24, 2019.

*Primary Examiner* — Thang X Le
(74) *Attorney, Agent, or Firm* — NORTON ROSE FULBRIGHT US LLP; Gerard Messina

(57) ABSTRACT

A method for determining an orientation of a movable device. The method includes the steps: determining an extent of the change of the orientation on the basis of data of at least one first sensor unit, comparing the extent to a predetermined threshold value, if the threshold value is exceeded, switching on a second sensor unit if it is in a switched-off state and determining the orientation with the aid of the first sensor unit and the second sensor unit, at an undershoot of the threshold value or if the extent is equal to the threshold value, switching off the second sensor unit, if it is in a switched-on state, and ascertaining the orientation with the aid of the first sensor unit.

13 Claims, 2 Drawing Sheets

(51) Int. Cl.
*A61B 5/11* (2006.01)
*A61B 5/00* (2006.01)

(58) Field of Classification Search
CPC ...... G01C 9/00; G01C 17/28; G01C 19/5783; G01C 23/00
See application file for complete search history.

(56) References Cited

U.S. PATENT DOCUMENTS

| | | | |
|---|---|---|---|
| 2016/0245665 A1* | 8/2016 | Logan | G06K 19/027 |
| 2017/0026800 A1* | 1/2017 | Kim | H04W 4/80 |
| 2021/0141447 A1* | 5/2021 | Bichler | G06F 3/012 |

* cited by examiner

METHOD FOR DETERMINING AN ORIENTATION OF A MOVABLE DEVICE

FIELD

The present invention relates to a method for determining an orientation of a movable device.

Although the present invention is generally applicable to movable devices, the present invention is explained with reference to an intelligent device that is portable by a person.

BACKGROUND INFORMATION

Due to the emergence of portable intelligent devices, so-called "wearables," sensors, for example, acceleration sensors, pulse sensors, temperature sensors, or the like are also used in these small devices. If such a device is carried on the wrist, for example, a number of steps which the person has taken may be ascertained using the device, for example, or if such a device is carried on the wrist, for example, the position of a tennis racket, held with the hand, may be ascertained for movement analysis or the like.

SUMMARY

In one specific embodiment, the present invention provides a method for determining an orientation of a movable device, including the steps
  determining an extent of the change of the orientation on the basis of data of at least one first sensor unit,
  comparing the extent to a predefined threshold value,
  if the threshold value is exceeded, switching on a second sensor unit if it is in a switched-off state and ascertaining the orientation with the aid of the first sensor unit and the second sensor unit,
  at an undershoot of the threshold value or if the extent is equal to the threshold value, switching off the second sensor unit, if it is in a switched-on state, and ascertaining the orientation with the aid of the first sensor unit.

In a further specific embodiment, the present invention provides a movable device, including a first sensor unit, a second sensor unit, and an ascertainment unit, the first and second sensor units each being designed to provide data for a determination of the orientation, the ascertainment unit being designed to ascertain an extent of the change of the orientation of the device and if the extent of the change of the orientation exceeds a threshold value, to switch on the second sensor unit, if it is in a switched-off state, and then ascertaining the orientation with the aid of data of the first sensor unit and the second sensor unit and at an undershoot of the threshold value or if the extent is equal to the threshold value, switching off the second sensor unit, if it is in a switched-on state, and then ascertaining the orientation with the aid of the first sensor unit.

One of the advantages thus achieved is that the orientation of a movable device is energy-efficient and may be determined with high accuracy as a function of the present change of the orientation of the particular device. Another advantage is the lower power consumption overall.

Further features, advantages, and further specific embodiments of the present invention are described hereinafter or are thus apparent based on the disclosure herein.

According to one advantageous refinement of the present invention, the extent of the change of the orientation is ascertained on the basis of at least two temporally successive acceleration vectors ascertained with the aid of the first sensor unit. This enables an ascertainment of an orientation change on the basis of acceleration values in a simple and simultaneously reliable manner.

According to a further advantageous refinement of the present invention, the extent of the change of the orientation is ascertained on the basis of at least two temporally successive magnetic field vectors ascertained with the aid of the first sensor unit. This enables an ascertainment of an orientation change on the basis of magnetic field values in a simple and simultaneously reliable manner.

According to a further advantageous refinement of the present invention, the orientation of the particular angle between the at least two temporally successive vectors is determined for the determination of the extent of the change of the orientation. This enables a reliable and simultaneously simple determination of the extent of the change of the orientation.

According to a further advantageous refinement of the present invention, the orientation is ascertained on the basis of the first and the second sensor units for initialization. One of the advantages thus achieved is that the orientation is ascertained once in a particularly reliable way at the beginning of carrying the device, so that a change of the orientation may also be ascertained in a reliable way.

According to a further advantageous refinement of the present invention, if it is established that the threshold value is exceeded at a first point in time, the extent of the change of the orientation is ascertained on the basis of the first and second sensor units at a second point in time. An already switched-on second sensor unit may thus be used to determine the extent of the change of the orientation, which increases the accuracy of the determination of the change of the orientation overall.

According to a further advantageous refinement of the present invention, the threshold value of a change of the orientation corresponds to a rotation rate change between 10°/s and 60°/s, preferably between 20°/s and 50°/s, in particular between 25°/s and 40°/s, preferably 30°/s. In this way, a particularly energy-efficient and simultaneously reliable determination of the change of the orientation is enabled.

According to one advantageous refinement of the example device, the first sensor unit includes an acceleration sensor and/or a magnetometer. A change of the orientation may thus be ascertained in a particularly energy-efficient way on the basis of data of the particular sensor or sensors.

According to a further advantageous refinement of the device, the second sensor unit includes a rotation rate sensor. A change of the orientation may be determined particularly reliably and precisely in this way.

Further important features and advantages of the present invention result from the figures, and from the associated description of the figures on the basis of the figures.

It shall be understood that the above-mentioned features and the features still to be explained hereinafter are usable not only in the particular specified combination but rather also in other combinations or in a unique position, without departing from the scope of the present invention.

Preferred designs and specific embodiments of the present invention are shown in the figures and explained in greater detail below, identical reference numerals referring to identical or similar or functionally identical components or elements.

DETAILED DESCRIPTION OF EXAMPLE EMBODIMENTS

Figure 1:
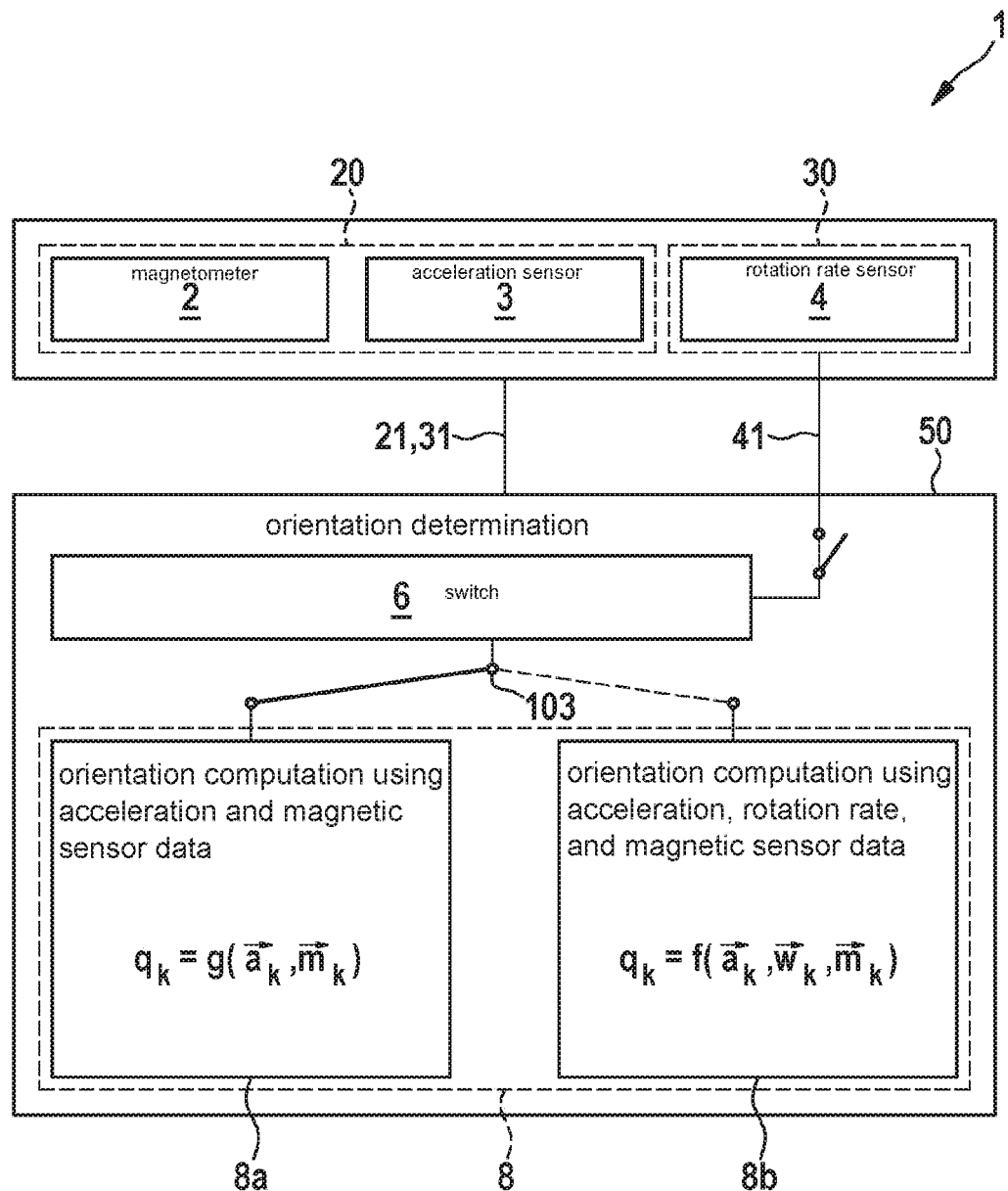
FIG. 1 shows a device according to one specific embodiment of the present invention.

FIG. 1 shows a device according to one specific embodiment of the present invention.

In detail, a block diagram of a device according to one specific embodiment of the present invention is shown in FIG. 1. In this case, present acceleration values $\vec{a}$, sensor data 31, magnetic field values $\vec{m}$, sensor data 21, and optionally rotation rate values $\vec{w}$, sensor data 41, are determined in all three spatial axes, i.e., the x, y, and z axes, via an acceleration sensor 3, a magnetometer 2, and a rotation rate sensor 4. These sensor data 21, 31, 41 are subsequently used by a function f $$q_k = f(\vec{a}_k, \vec{w}_k, \vec{m}_k)$$

or g $$q_k = g(\vec{a}_k, \vec{m}_k)$$

to determine orientation $q_k$ at a discrete point in time k. Decision 103 as to whether function f, reference numeral 8a or function g, reference numeral 8b is used is ascertained by a switch 6 of a switching unit 50, which receives sensor data 21, 31, 41 to ascertain the orientation.

Figure 2:
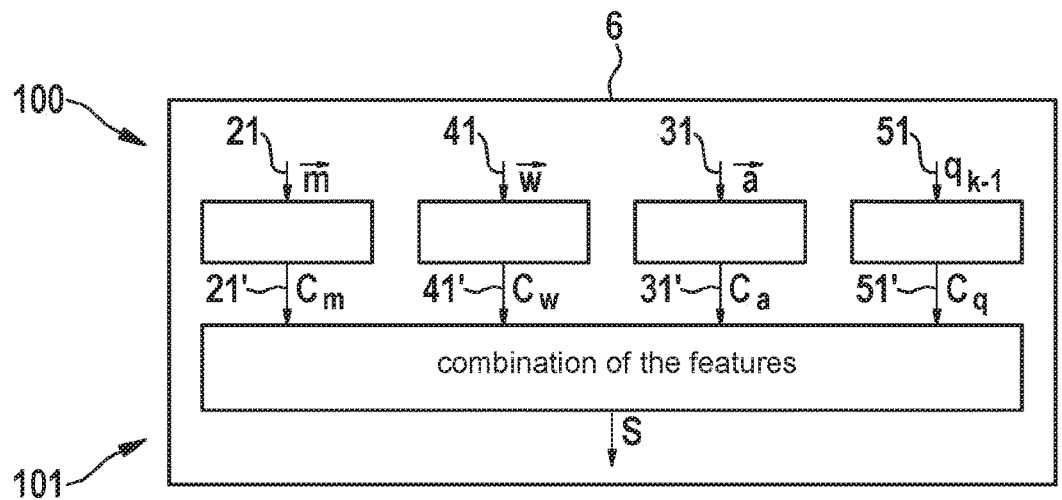
FIG. 2 shows a part of the device according to one specific embodiment of the present invention.

FIG. 2 shows a part of a device according to one specific example embodiment of the present invention.

A structure of switch 6 and its functionality is shown in FIG. 2. On the basis of orientation $q_{k-1}$, reference numeral 51, and sensor data $\vec{a}$, $\vec{m}$, and optionally $\vec{w}$, reference numerals 21, 31, 41, it is ascertained by switch 6 whether function f, reference numeral 8b, or g, reference numeral 8a, is used for the determination of orientation $q_k$. The orientation is shown here by way of example as a quaternion. A quaternion $q_k$ is a type of position indication, which is distinguished from the so-called Euler angles in that the problem of the so-called gimbal lock may be bypassed. Depending on the application, however, another position indication, for example, in Euler angles, may also be used instead of the quaternion $q_k$. If function f 8b, i.e., a fusion of rotation rate, acceleration, and magnetic field data 21, 31, 41 is selected, rotation rate sensor 4 is activated. If function g 8a, i.e., a fusion of only acceleration and magnetic field data 21, 31 is selected, rotation rate sensor 4 is deactivated. The selection of which function f 8b or g 8a is to be selected is based on different variables which are described hereinafter as Boolean variables 21', 31', 41', 51'. A combination of the variables is also possible here.

To be able to ascertain a change of the orientation within acceleration data 31, the angle which results between two successive acceleration vectors may be determined. The angle between two vectors may be computed with the aid of the known formula:

$$\sin\alpha = \frac{|\vec{a}_k \times \vec{a}_{k-1}|}{|\vec{a}_k \cdot \vec{a}_{k-1}|}$$

If the angle $\sin\alpha$ is greater than a threshold value $\tau_a$ to be established, a significant change of the orientation may be assumed. Angle α thus forms an extent S of the change of the orientation.

$$C_a = \begin{cases} \text{FALSE, if } \sin a < \tau_a \\ \text{TRUE, if } \sin a \geq \tau_a \end{cases}$$

Boolean variable $C_a$, reference numeral 31' may thus be set to the value TRUE, on the basis of which switch 6 in the later procedure selects function f 8b for the determination of quaternion $q_k$, i.e., the orientation, and activates rotation rate sensor 4. Instead of the decision on the basis of two successive acceleration vectors 31, the evaluation on the basis of filtered and/or processed acceleration values or data or a predefined time interval is also possible. In the case of a defined time interval, two successive measured values $a_k$ and $a_{k-1}$ are not used directly for computing the angle, but rather the angle between $a_k$ and $a_{k-n}$ is determined, index k standing for the present point in time and n standing for a whole number greater than 0, which describes a point in time in the past.

In order to alternatively or additionally be able to ascertain a change of the orientation within magnetic field data 21, the angle which results between two successive magnetic field vectors may be determined similarly to the variable provided above from acceleration data 31.

$$\sin\gamma = \frac{|\vec{m}_k \times \vec{m}_{k-1}|}{|\vec{m}_k \cdot \vec{m}_{k-1}|}$$

If angle $\sin\gamma$ is greater than a threshold value $\tau_m$ to be established, a significant change of the orientation may be assumed. Angle γ thus forms an extent S of the change of the orientation.

$$C_m = \begin{cases} \text{FALSE, if } \sin\gamma < \tau_m \\ \text{TRUE, if } \sin\gamma \geq \tau_m \end{cases}$$

Boolean variable $C_m$ 21' may thus be set to the value TRUE. Similarly to the variables based on acceleration data 31, instead of the decision on the basis of two successive magnetic field vectors 21, the evaluation may also be carried out on the basis of filtered and/or processed magnetic field values or data of a predefined time interval.

Various methods may be applied to be able to ascertain a change of the orientation on the basis of measured data 41 of rotation rate sensor 4. The calculation of a Boolean variable $C_w$ 41' and a further Boolean variable $C_{\Delta w}$ are provided in the following. The variables differ in that once the Euclidean norm of measured rotation rate vector $\vec{w}_k$ is used to determine the variables and once the Euclidean norm Δw. The Euclidean norm of the change of the rotation rate may be determined via the formula:

$$\Delta w = \left\| \frac{\vec{w}_k - \vec{w}_{k-1}}{\Delta T} \right\|$$

If the Euclidean norm of the change of the rotation rate is greater than threshold value $\tau_{\Delta w}$, a significant change of the orientation may be assumed.

$$C_{\Delta w} = \begin{cases} \text{FALSE, if } \Delta w < \tau_{\Delta w} \\ \text{TRUE, if } \Delta w \geq \tau_{\Delta w} \end{cases}$$

Variable $C_{\Delta w}$ may thus be set to the value TRUE. Alternatively, it may be checked whether the Euclidean norm of rotation rate $\vec{w}_k$ is greater than a threshold value $\tau_w$.

$$C_w = \begin{cases} \text{FALSE, if } \|\vec{w}_k\| < \tau_w \\ \text{TRUE, if } \|\vec{w}_k\| \geq \tau_w \end{cases}$$

If the Euclidean norm of rotation rate $\vec{w}_k$ is less than threshold value $\tau_w$, variable $C_w$ 41' may be set to FALSE. Variables on the basis of rotation rates may be used here for the transition of the state having a high dynamic orientation changes to the state having low dynamic state changes, because rotation rate sensor 4 is deactivated in the state having low dynamic state changes and thus cannot provide sensor data 41.

In addition to the data of sensors 21, 31, 41, quaternion q, which is ascertained by functions f 8b and g 8a, may also be used for computing a variable 51'. The change of the orientation between point in time k-1 and point in time k-2, reference numeral 51, may be ascertained for this purpose, for example, via a quaternion multiplication:

$$\Delta q_{k-1} = q_{k-1} * q_{k-2}$$

If normed quaternion $\Delta q$ is represented as a vector:

$$\Delta q = \begin{pmatrix} \cos(\frac{\varphi}{2}) \\ x \cdot \sin(\frac{\varphi}{2}) \\ y \cdot \sin(\frac{\varphi}{2}) \\ z \cdot \sin(\frac{\varphi}{2}) \end{pmatrix} \text{ with } x, y, z \in \mathbb{R}$$

normed vector (x, y, z) may be understood as a rotational axis and $\varphi$ as a rotational angle. The normal or the absolute value of rotational angle $|\varphi|$ thus contains an extent S of the change of the orientation, on the basis of which a Boolean variable 51' may be defined:

$$C_q = \begin{cases} \text{FALSE, if } |\varphi| < \tau_\varphi \\ \text{TRUE, if } |\phi| \geq \tau_\varphi \end{cases}$$

If the rotational angle is greater than a threshold value $\tau_\varphi$, a significant change of the orientation may be assumed.

A combination S of Boolean variables 21', 31', 41', 51' may be carried out in various ways. One option, for example, is to carry out a logical AND linkage of ascertained Boolean variables 21', 31', 41', 51', if this provides logical output values as described above by way of example. However, other combinations of Boolean variables 21', 31', 41', 51' are also possible, for example, on the basis of probability densities or neural networks.

$$S = C_q \& C_w \& C_m \& C_a$$

If value S is TRUE, subsequently function f 8b is used and a fusion of rotation rate, magnetic sensor, and acceleration data 21, 31, 41 is carried out.

If value S is FALSE, subsequently function g 8a is used and the orientation is only ascertained on the basis of acceleration sensor and magnetometer data 21, 31 and rotation rate sensor 4 is deactivated.

Figure 3:
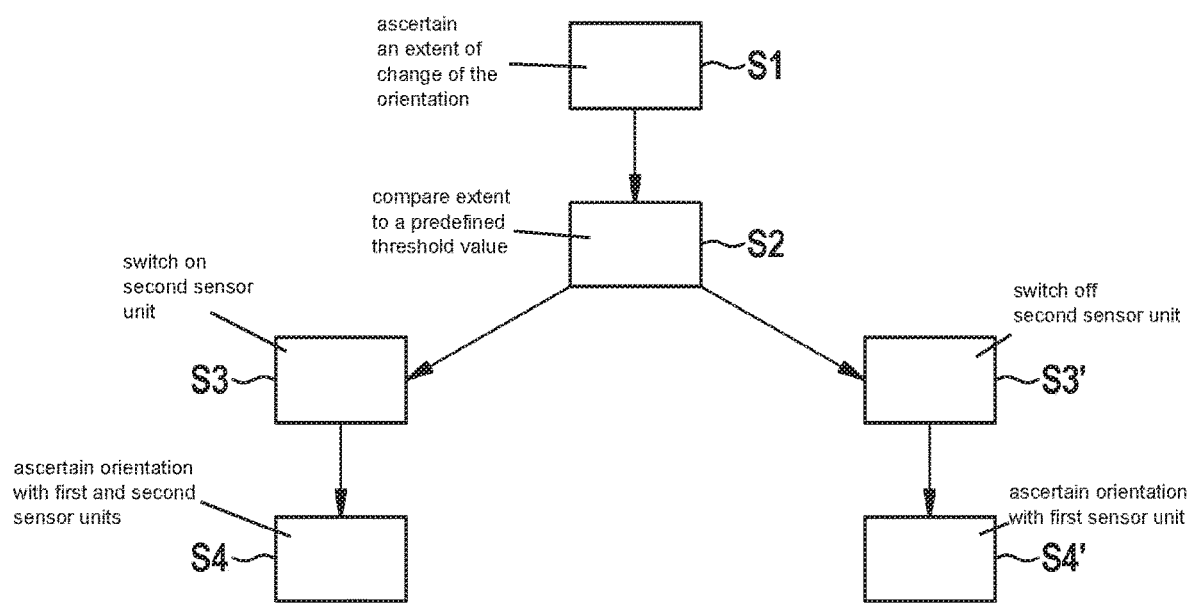
FIG. 3 shows a method according to one specific embodiment of the present invention.

FIG. 3 shows a method according to one specific example embodiment of the present invention.

In a first step, an ascertainment S1 of an extent S of the change of the orientation is carried out on the basis of data 21, 31 of at least one first sensor unit 20.

In a second step S2, a comparison of extent S to a predefined threshold value takes place.

In a third step S3, if the threshold value is exceeded, a second sensor unit 30 is switched on, if it is in a switched-off state.

In a fourth step S4, the orientation is ascertained with the aid of first sensor unit 20 and second sensor unit 30.

In an alternative third step S3', at an undershoot of the threshold value or if the extent S is equal to the threshold value, second sensor unit 30 is switched off if it is in a switched-on state.

In an alternative fourth step S4', the orientation is ascertained with the aid of first sensor unit 20.

In summary, at least one of the specific example embodiments of the present invention includes at least one of the following advantages:

Simple implementation.
Low power consumption.
Reliable ascertainment of the orientation.

Although the present invention is described herein on the basis of preferred exemplary embodiments, it is not restricted thereto, but rather is modifiable in manifold ways.

What is claimed is:

1. A method for determining an orientation of a movable device, comprising the following steps:
   ascertaining an extent of a change of the orientation based on data of at least one first sensor unit including an acceleration sensor and a magnetometer;
   comparing the extent to a predefined threshold value;
   when the threshold value is exceeded: (i) switching on a second sensor unit including a rotation rate sensor if the rotation rate sensor is in a switched-off state, and (ii) ascertaining the orientation using the first sensor unit and the second sensor unit;
   at an undershoot of the threshold value or when the extent is equal to the threshold value: (i) switching off the second sensor unit if the second sensor unit is in a switched-on state, and (ii) ascertaining the orientation using the first sensor unit and not the second sensor unit.

2. The method as recited in claim 1, wherein the extent of the change of the orientation is ascertained based on at least two temporally successive acceleration vectors ascertained using the first sensor unit.

3. The method as recited in claim 1, wherein the extent of the change of the orientation is ascertained based on at least two temporally successive magnetic field vectors ascertained using the first sensor unit.

4. The method as recited in claim 2, wherein a particular angle between the at least two temporally successive acceleration vectors is ascertained for the determination of the extent of the change of the orientation.

5. The method as recited in claim 3, wherein a particular angle between the at least two temporally successive magnetic field vectors is ascertained for the determination of the extent of the change of the orientation.

6. The method as recited in claim 1, wherein the orientation is ascertained using the first sensor unit and the second sensor unit for initialization.

7. The method as recited in claim 1, wherein when it is established that the threshold value is exceeded at a first point in time, the extent of the change of the orientation is ascertained based on data of the first sensor unit and the second sensor unit at a second point in time.

8. The method as recited in claim 1, wherein the threshold value of the change of the orientation corresponds to a rotation rate change between 10°/s and 60°/s.

9. The method as recited in claim 1, wherein the threshold value of the change of the orientation corresponds to a rotation rate change between 20°/s and 50°/s.

10. The method as recited in claim 1, wherein the threshold value of the change of the orientation corresponds to a rotation rate change between 25°/s and 40°/s.

11. The method as recited in claim 1, wherein the threshold value of the change of the orientation corresponds to a rotation rate change of 30°/s.

12. A movable device, comprising:
 a first sensor unit including an acceleration sensor and a magnetometer;
 a second sensor unit including a rotation rate sensor; and
 an ascertainment unit;
 wherein each of the first sensor unit and the second sensor unit being configured to provide data for determination of the orientation of the device;
 wherein the ascertainment unit is configured to ascertain an extent of the change of the orientation of the device, and (i) if a threshold value for the extent of the change of the orientation is exceeded, the ascertainment unit is configured to switch on the second sensor unit if the second sensor unit is in a switched-off state, and to ascertain the orientation using the data of the first sensor unit and the second sensor unit, and (ii) at an undershoot of the threshold value or if the extent is equal to the threshold value, the ascertainment unit is configured to switch off the second sensor unit if the second sensor unit is in a switched-on state, and to ascertain the orientation using the first sensor unit and not the second sensor unit.

13. The device as recited in claim 12, wherein the device is configured to be portable on a body of a person.

\* \* \* \* \*